US007781598B2

(12) United States Patent
Keegan et al.

(10) Patent No.: US 7,781,598 B2
(45) Date of Patent: Aug. 24, 2010

(54) PROCESS FOR THE PREPARATION OF SUBSTITUTED INDOLES

(75) Inventors: Philip Keegan, Leicestershire (GB); Eric Merifield, Leicestershire (GB); Duncan Gill, Leicestershire (GB)

(73) Assignee: AstraZeneca AB, Södertälje (SE)

( * ) Notice: Subject to any disclaimer, the term of this patent is extended or adjusted under 35 U.S.C. 154(b) by 476 days.

(21) Appl. No.: 11/813,816

(22) PCT Filed: Jan. 9, 2006

(86) PCT No.: PCT/GB2006/000060

§ 371 (c)(1),
(2), (4) Date: Jul. 12, 2007

(87) PCT Pub. No.: WO2006/075139

PCT Pub. Date: Jul. 20, 2006

(65) Prior Publication Data

US 2008/0051586 A1 Feb. 28, 2008

(30) Foreign Application Priority Data

Jan. 13, 2005 (GB) ................. 0500604.4

(51) Int. Cl.
*C07D 209/30* (2006.01)
*C07D 209/04* (2006.01)
*C07D 209/08* (2006.01)
(52) U.S. Cl. .................. 548/484; 548/469; 548/510
(58) Field of Classification Search .......... 548/548, 548/510, 484, 469
See application file for complete search history.

(56) References Cited

U.S. PATENT DOCUMENTS

| 5,459,150 | A | 10/1995 | Brooks et al. |
| 5,486,525 | A | 1/1996 | Summers, Jr. et al. |
| 5,567,711 | A | 10/1996 | Sheppard et al. |
| 6,916,841 | B2 | 7/2005 | Seehra et al. |
| 6,933,316 | B2 | 8/2005 | Hsieh et al. |
| 7,166,607 | B2 | 1/2007 | Bonnert et al. |
| 2005/0222201 | A1 | 10/2005 | Birkinshaw et al. |
| 2006/0111426 | A1 | 5/2006 | Bonnert et al. |
| 2006/0264444 | A1 | 11/2006 | Bonnert et al. |
| 2008/0027092 | A1 | 1/2008 | Bonnert et al. |
| 2008/0051586 | A1 | 2/2008 | Keegan et al. |
| 2008/0249110 | A1 | 10/2008 | Bonnert et al. |
| 2009/0143449 | A1 | 6/2009 | Bonnert et al. |
| 2009/0163518 | A1 | 6/2009 | Bonnert et al. |

FOREIGN PATENT DOCUMENTS

| EP | 0254241 | 1/1988 |
| EP | 0530907 | 3/1993 |
| EP | 0576347 | 12/1993 |
| EP | 0 924 209 | 6/1999 |
| EP | 1170594 | 1/2002 |
| EP | 1505061 | 2/2005 |
| GB | 1356834 | 6/1974 |
| GB | 2422831 | 8/2006 |
| WO | WO 94/19321 | 9/1994 |
| WO | WO 95/16687 | 6/1995 |
| WO | WO 98/13368 | 4/1998 |
| WO | WO 99/09007 | 2/1999 |
| WO | WO 00/78761 | 12/2000 |
| WO | WO 01/32621 | 5/2001 |
| WO | WO 01/47922 | 7/2001 |
| WO | WO 01/92224 | 12/2001 |
| WO | WO 03/064387 | 8/2003 |
| WO | WO 03/066046 | 8/2003 |
| WO | WO 03/066047 | 8/2003 |
| WO | WO 03/097598 | 11/2003 |
| WO | WO 03/101961 | 12/2003 |
| WO | WO 03/101981 | 12/2003 |
| WO | WO 2004/007451 | 1/2004 |
| WO | WO 2004/016609 | 2/2004 |
| WO | WO 2004/106302 A1 | 12/2004 |
| WO | WO 2005/019171 | 3/2005 |
| WO | WO 2005/040114 | 5/2005 |
| WO | WO 2005/054232 | 6/2005 |
| WO | WO 2006/075139 | 7/2006 |
| WO | WO 2007/138282 | 12/2007 |
| WO | WO 2007/140786 | 12/2007 |
| WO | WO 2008/000409 | 1/2008 |

OTHER PUBLICATIONS

Atkinson et al., "A New Synthesis of 3-Arylthioindoles", *Synthesis* 6:480-481 (1988).
Cecil Textbook of Medicine, 20th edition, vol. 2:1992-1996 (1996).
Cecil Textbook of Medicine, 20th edition, vol. 2:2050-2057 (1996).
FDA mulls drug to slow late-stage Alzheimer's [online], [retrieved on Sep. 23, 2003]. Retrieved from the Internet, URL:http://www.cnn.com/2003/HEALTH/conditions/09/24/alzheimers.drug.ap/indexhtml>.
Database CA 'Online! Chemical Abstracts Service, Columbus, Ohio, US; Tanimoto, Norihiko et al: "Preparation of indole derivatives as PGD2 receptor antagonists" XP002301963 retrieved from STN Database accession No. 2003:931327.
Garcia et al., "A Novel Synthesis of 3-Cyanoindoles and a New Route to Indole-3-Carboxylic Acid Derivatives", *Tetrahedron Letters* 26(15):1827-1830 (1985).
Hamel et al., "Regioselective Synthesis of Mixed Indole 2,3-Bis-(sulfides). A Study of the Mechanism of the Second Sulfenylation of Indole", *J. Org. Chem.* 61:1573-1577 (1996).
Hary et al., "Efficient synthesis of 3-(4,5-dihydro-1*H*-imidazole-2-yl)-1*H*-indoles", *Tetrahedron Letters* 42:5187-5189 (2001).

(Continued)

*Primary Examiner*—Rebecca L Anderson
*Assistant Examiner*—Jason M Nolan
(74) *Attorney, Agent, or Firm*—Fish & Richardson P.C.

(57) ABSTRACT

The invention relates to a novel process for the preparation of substituted indoles which are useful as therapeutic agents.

8 Claims, No Drawings

OTHER PUBLICATIONS

Howard et al., "Synthesis and aldose reductase inhibitory activity of substituted 2(1*H*)-benzimidazolone- and oxindole-1 -acetic acids", *Eur J Med Chem* 27:779-789 (1992).

Lüscher et al., "Deblocking of *o*-Nitrophenylsulfenyl-Protected Peptides by Ammonium Thiocyanate and (2-Methyl-1-indolyl) acetic acid", *Helv. Chim. Acta* 66(2):602-605 (1983).

Matassa et al., "Evolution of a Series of Peptidoleukotriene Antagonists: Synthesis and Structure/Activity Relationships of 1,3,5-Substituted Indoles and Indazoles", *J. Med. Chem.* 33:1781-1790 (1990).

Matsugi et al., "An efficient sylfenylation of aromatics using highly active quinone mono *O,S*-acetal bearing a pentafluorophenylthio group", *Tetrahedron Letters* 42:1077-1080 (2001).

Matsugi et al., "Facile and Efficient Sulfenylation Method Using Quinone Mono-*O,S*-Acetals under Mild Conditions", *J. Org. Chem.* 66:2434-2441 (2001).

Morissette et al., "High-throughput crystallization: polymorphs, salts, co-crystals and solvates of pharmaceutical solids", *Advanced Drug Delivery Reviews* 56:275-300 (2004).

Ovenden et al., "Echinosulfonic Acids A-C and Echinosulfone A: Novel Bromoindole Sulfonic Acids and a Sulfone from a Southern Australian Marine Sponge, *Echinodictyum*", *J. Nat. Prod.* 62:1246-1249 (1999).

Patani and LaVoie, "Bioisosterism: A Rational Approach in Drug Design", *Chem Rev.* 96:3147-3176 (1996).

STN International, CAPLUS accession No. 1977:535057, Document No. 87:135057, Sankyo Co., Ltd., "3-Indolyl thio ethers", & JP,A2,52039671, 19770328, RN 64137-76-4, 54491-43-9, 56366-45-1.

STN International, CAPLUS accession No. 1980:6356, Document No. 92:6356, Gabrielyan, G.E. et al.: "Indole derivatives. LX. Synthesis of indole compounds with a furan ring", & Armyanskii Khimicheskii Zhurnal (1979), 32(4), 309-14, RN 51842-57-0.

STN International, CAPLUS accession No. 2001:235566, Document No. 134:266203, Kato, Susumu et al.: "Preparation and application of benzopyranone derivatives"; & JP,A2,2001089471, 20010403, RN 332082-10-7.

STN International, CAPLUS accession No. 2001:338492, Document No. 134:353315, Wakunaga Pharmaceutical Co., Ltd., "Preparation of indole derivatives as chymase inhibitors and drugs containing the same as the active ingredient", & WO,A1,2001032621, 20010510, RN 64137-76-4, 336186-33-5.

STN International, CHEMCATS accession No. 2000:1027702, Apr. 26, 2001, 8004-3013, "1H-Indole-1-acetic acid, 2-methyl-3-(phenylthio)-, ethyl esther", CAS Registry No. 300860-50-8.

STN International, file CAPLUS, CAPUS accession No. 1995:401159, Document No. 122:187576, Yoshitomi Pharmaceutical Industries, Ltd., "Preparation of fused pyrazole derivatives", & JP,A2,06206872, 19940726.

Vippagunta et al., abstract, "Crystalline solids", *Advanced Drug Delivery Reviews* 48:3-26 (2001).

"COPD: Causes and Prevention." NIH SeniorHealth. National Heart, Lung, and Blood Institute. Accessed Apr. 6, 2009. <http://nihseniorhealth.gov/copd/causesandprevention/01.html>.

"Prevention of Cystic Fibrosis." WrongDiagnosis.com. Accessed Apr. 6, 2009. <http://www.wrongdiagnosis.com/c/cf/prevent.htm>.

USPTO Non-Final Office Action in U.S. Appl. No. 10/516,557, mailed Mar. 2, 2006, 11 pages.

Fish & Richardson P.C., Amendment in Reply to Action of Mar. 2, 2006 in U.S. Appl. No. 10/516,557, filed Jun. 1, 2006, 8 pages.

USPTO Notice of Allowance in U.S. Appl. No. 10/516,557, mailed Aug. 21, 2006, 9 pages.

Fish & Richardson P.C., Response to Notice of Allowance of Aug. 21, 2006 in U.S. Appl. No. 10/516,557, filed Nov. 20, 2006, 2 pages.

USPTO Non-Final Office Action in U.S. Appl. No. 10/516,165, mailed Apr. 30, 2008, 8 pages.

Fish & Richardson P.C., Reply to Action of Apr. 30, 2008 in U.S. Appl. No. 10/516,165, filed Jul. 30, 2008, 13 pages.

USPTO Notice of Allowance in U.S. Appl. No. 10/516,165, mailed Nov. 18, 2008, 7 pages.

Fish & Richardson P.C., RCE/IDS in reply to Notice of Allowance of Nov. 18, 2008 in U.S. Appl. No. 10/516,165, filed Feb. 18, 2009, 3 pages.

USPTO Notice of Allowance in U.S. Appl. No. 10/516,165, mailed Apr. 2, 2009, 8 pages.

Fish & Richardson P.C., RCE/IDS in reply to Notice of Allowance of Apr. 2, 2009 in U.S. Appl. No. 10/516,165, filed Jul. 2, 2009, 4 pages.

USPTO Notice of Allowance in U.S. Appl. No. 10/516,165, mailed Oct. 5, 2009, 8 pages.

Fish & Richardson P.C., RCE/IDS in reply to Notice of Allowance of Oct. 5, 2009 in U.S. Appl. No. 10/516,165, filed Nov. 13, 2009, 4 pages.

USPTO Notice of Allowance in U.S. Appl. No. 10/516,165, mailed Dec. 15, 2009, 8 pages.

USPTO Non-Final Office Action in U.S. Appl. No. 10/521,325, mailed Jan. 9, 2007, 32 pages.

Fish & Richardson P.C., Amendment in Reply to Action of Jan. 9, 2007 in U.S. Appl. No. 10/521,325, filed Jul. 9, 2007, 15 pages.

USPTO Final Office Action in U.S. Appl. No. 10/521,325, mailed Oct. 15, 2007, 6 pages.

Fish & Richardson P.C., RCE/IDS and Amendment in Reply to Action of Oct. 15, 2007 in U.S. Appl. No. 10/521,325, filed Feb. 21, 2008, 13 pages.

USPTO Non-Final Office Action in U.S. Appl. No. 10/521,325, mailed May 1, 2008, 35 pages.

Fish & Richardson P.C., Amendment in Reply to Action of May 1, 2008 in U.S. Appl. No. 10/521,325, filed Aug. 1, 2008, 10 pages.

USPTO Non-Final Office Action in U.S. Appl. No. 10/521,325, mailed Nov. 14, 2008, 8 pages.

Fish & Richardson P.C., Amendment in Reply to Action of Nov. 14, 2008 in U.S. Appl. No. 10/521,325, filed Mar. 13, 2009, 14 pages.

USPTO Final Office Action in U.S. Appl. No. 10/521,325, mailed Jul. 9, 2009, 9 pages.

Fish & Richardson P.C., RCE/IDS and Amendment in Reply to Action of Jul. 9, 2009 in U.S. Appl. No. 10/521,325, filed Oct. 9, 2009, 14 pages.

USPTO Notice of Allowance in U.S. Appl. No. 10/521,325, mailed Jan. 12, 2010, 9 pages.

USPTO Non-Final Office Action in U.S. Appl. No. 10/558,228, mailed Jan. 9, 2009, 25 pages.

Fish & Richardson P.C., Amendment in Reply to Action of Jan. 9, 2009 in U.S. Appl. No. 10/558,228, filed Mar. 5, 2009, 9 pages.

USPTO Notice of Allowance in U.S. Appl. No. 10/558,228, mailed May 19, 2009, 8 pages.

Fish & Richardson P.C., RCE/IDS in reply to Notice of Allowance of May 19, 2009 in U.S. Appl. No. 10/558,228, filed Aug. 19, 2009, 5 pages.

USPTO Notice of Allowance in U.S. Appl. No. 10/558,228, mailed Nov. 3, 2009, 8 pages.

Fish & Richardson P.C., Response to Notice of Allowance of Nov. 3, 2009 in U.S. Appl. No. 10/558,228, filed Feb. 2, 2010, 2 pages.

USPTO Notice of Allowance in U.S. Appl. No. 10/568,889, mailed Oct. 16, 2008, 16 pages.

Fish & Richardson P.C., RCE/IDS in reply to Notice of Allowance of Oct. 16, 2008 in U.S. Appl. No. 10/568,889, filed Jan. 16, 2009, 4 pages.

USPTO Non-Final Office Action in U.S. Appl. No. 10/568,889, mailed Mar. 23, 2009, 18 pages.

Fish & Richardson P.C., Amendment in Reply to Action of Mar. 23, 2009 in U.S. Appl. No. 10/568,889, filed Jun. 18, 2009, 13 pages.

USPTO Notice of Allowance in U.S. Appl. No. 10/568,889, mailed Sep. 9, 2009, 9 pages.

Fish & Richardson P.C., RCE/IDS in reply to Notice of Allowance of Sep. 9, 2009 in U.S. Appl. No. 10/568,889, filed Nov. 13, 2009, 4 pages.

USPTO Notice of Allowance in U.S. Appl. No. 10/568,889, mailed Dec. 3, 2009, 9 pages.

USPTO Non-Final Office Action in U.S. Appl. No. 12/302,353, mailed Jun. 23, 2009, 34 pages.

Fish & Richardson P.C., Amendment in Reply to Action of Jun. 23, 2009 in U.S. Appl. No. 12/302,353, filed Sep. 23, 2009, 14 pages.

USPTO Notice of Allowance in U.S. Appl. No. 12/302,353, mailed Feb. 9, 2010, 11 pages.

PROCESS FOR THE PREPARATION OF SUBSTITUTED INDOLES

CROSS-REFERENCE TO RELATED APPLICATIONS

This application is a national phase application under 35 U.S.C. §371 of PCT International Application No. PCT/GB2006/000060, filed Jan. 9, 2006, which claims priority to United Kingdom Application Serial No, 0500604.4, filed Jan. 13, 2005. The contents of each at these is incorporated herein by reference.

The present invention relates to a novel process for the preparation of substituted indoles which are useful as therapeutic agents.

WO 04/106302 discloses a series of substituted indoles useful for the treatment of respiratory diseases.

New processes have now been developed for certain compounds which are more efficient than those disclosed in the art.

In a first aspect the invention therefore provides a process for the preparation of a compound of formula (I) or a pharmaceutically acceptable salt or solvate thereof:

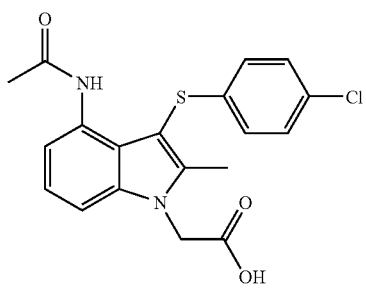

(I)

which comprises de-esterification of a compound of formula (II):

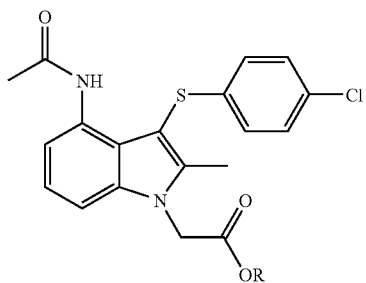

(II)

in which R is an ester forming group, and optionally thereafter forming a pharmaceutically acceptable salt or solvate.

The reaction can be carried out in the presence of a base followed by treatment with acid and a ketone or ester containing solvent or mixtures of said solvents or mixtures comprising said solvents. The compounds of formula (II) are treated with a base such as an alkali metal hydroxide in a suitable solvent such as an organic alcohol, preferably at elevated temperature. The reaction mixture is then treated with acid at elevated temperature in the presence of ketone or ester-containing solvents to give the compound of formula (I). The use of ketone and ester-containing solvents has surprisingly been found to promote crystal growth. Suitable solvents include ethyl acetate, n-propylacetate and MIBK and mixtures thereof. Preferably MIBK is used. Preferably the compound of formula (II) is treated with aqueous sodium hydroxide in n-propanol at elevated temperature, for example at about 68° C. Preferably the group R is phenyl, benzyl or a $C_{1-6}$alkyl group such as methyl or ethyl, preferably R is $C_{1-6}$alkyl, more preferably ethyl.

Compound of formula (II) are prepared by reaction of compounds of formula (III):

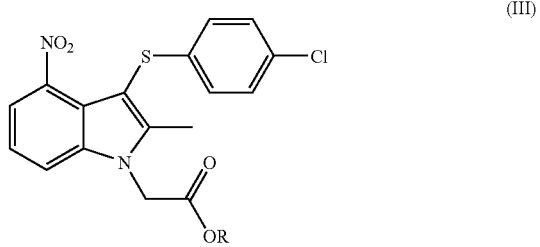

(III)

in which R is hydrogen or is as defined in formula (II) by hydrogenation followed by treatment of the resulting amine with an acetylating agent such as acetyl chloride. Preferably R is an ester forming group as defined in formula (II). The hydrogenation can be carried out using standard conditions such as using a platinum catalyst under a hydrogen atmosphere at elevated pressure, e.g. a pressure of about 4 bar. This reduction can also be achieved with sodium dithionite. The resulting amine, which is optionally isolated, for example by crystallisation from ethyl acetate/iso-hexane, is treated with acetyl chloride in a solvent such as ethyl acetate at ambient or elevated temperature, preferably at about 40° C.

Compounds of formula (III) can be prepared by reacting compounds of formula (IV):

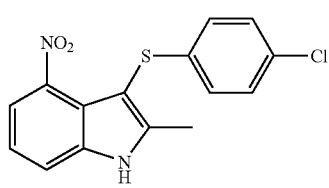

(IV)

with compounds of formula (V):

XCH$_2$CO$_2$R  (V)

in which R is as defined in formula (II) and X is halogen. Preferably R is ethyl and X is bromo such that the compound (V) is ethylbromoacetate. The reaction is carried out in the presence of a base such as potassium carbonate in water/acetonitrile.

Compounds of formula (IV) can be prepared by reacting compounds of formula (VI):

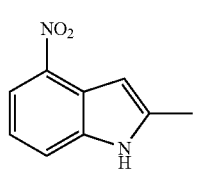

(VI)

with compounds of formula (VII):

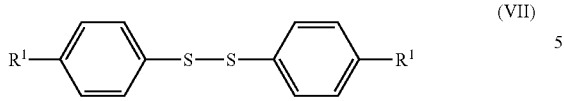

in which R[1] is chloro or a group that be converted to chloro such as amino or hydrogen. Preferably R[1] is chloro. The reaction of compounds (VI) and (VII) can be carried out using a suitable base such as sodium methoxide in methanol at elevated temperature, or a reagent such as trichloroisocyanuric acid in a solvent such as ethyl acetate or dichloromethane.

In an alternative embodiment of the invention compounds of formula (II) can be prepared from compounds of formula (VIII):

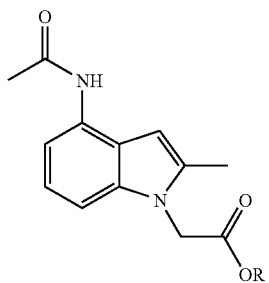

in which R is hydrogen or is as defined in formula (II) by reacting with a compound of formula (VII). The reaction can be carried out using trichloroisocyanuric acid as described above. This reaction is advantageous where R is hydrogen as it can be used for the direct preparation of compounds of formula (I).

Compounds of formula (VII) can be prepared from compounds of formula (IX):

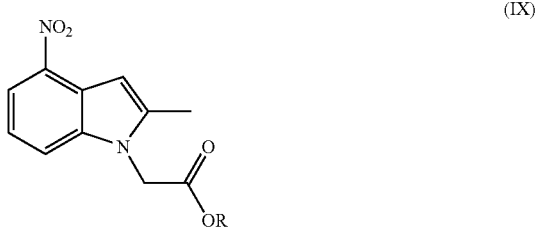

in which R is hydrogen or is as defined in formula (II) by hydrogenation and subsequent reaction of the resulting amine using analogous conditions to those described above for the hydrogenation of compound (V). Preferably R is as defined in formula (II), more preferably R is ethyl.

Compound (IX) can be prepared from a compound of formula (VI) by reaction with a compound such as ethylbromoacetate using analogous conditions to those described above for the reaction of compound (IV).

In a still further embodiment of the invention compounds of formula (III) can be prepared from compounds of formula (IX) as defined above by reacting with a compound of formula (VII) as defined above using analogous conditions to those described above for the reaction of compounds (VI) and (VII) using TCCA.

All novel intermediates disclosed herein form a farther aspect of the invention. In a further aspect the invention therefore provides a compound of formula (VIII) and (IX).

The following examples illustrate the invention.

EXAMPLE 1

3-(4-Chlorophenylsulfanyl)-2-methyl-4-nitro-1H-indole

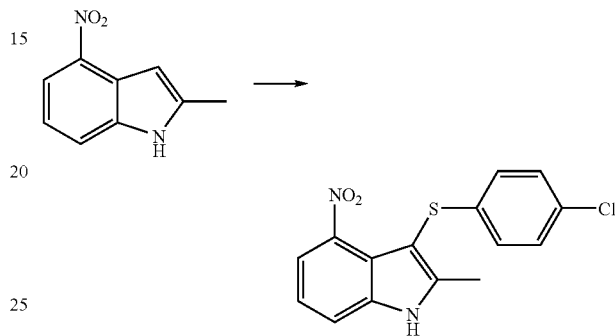

Method A

Sodium methoxide in methanol (4.1 kg, 25% w/w, 19 mol) was added to a stirred suspension of 2-methyl-4-nitro-1H-indole (1.52 kg, 8.6 mol) and bis(p-chlorophenyl)disulphide (2.48 kg, 8.6 mol) in methanol (6.47 kg) followed by a methanol line rinse (0.67 kg). The mixture was then heated at 60-65° C. for 3.5 hours. Water (6.1 kg) was added to the reaction mixture, which was then cooled to 20° C. and stirred at this temperature for 7 minutes. The solid was collected by filtration, washed with water (2×4 kg) followed by ethyl acetate (2×4 kg) then dried in a vacuum oven at 40° C. 3-(4-Chlorophenylsulfanyl)-2-methyl-4-nitro-1H-indole was obtained as a bright yellow solid, 2.57 kg (93% yield).

$^1$H NMR (400 MHz, D$_6$-DMSO) δ 7.77 (d, J=7.9 Hz, 1H), 7.63 (d, J=7.6 Hz, 1H), 7.27 (m, 3H), 6.92 (d, J=8.8 Hz, 2H), 2.48 (s, 3H).

LC-MS (ES+): 319 (100%, MH+).

Method B

Trichloroisocyanuric acid (450 mg, 1.9 mmol) was added to a solution of bis(p-chlorodiphenyl)disulphide (1.63 g, 5.7 mmol) in ethyl acetate (10 ml) at ambient temperature, resulting in the formation of an orange suspension. After stirring at ambient temperature for 30 minutes, a suspension of 2-methyl-4-nitro-1H-indole (2.0 g, 11.3 mmol) in ethyl acetate (10 ml) was added followed by an ethyl acetate rinse (4 ml), using water bath cooling to control the mild exotherm. Stirring was continued at ambient temperature for 40 minutes. Aqueous sodium bicarbonate (5%, 20 ml) and water (20 ml) were added and the resulting suspension stirred at ambient temperature for 45 minutes. The solid was collected by filtration, washed with water (2×10 ml), followed by ethyl acetate (2×10 ml) then dried in a vacuum oven at 45° C. to provide 3-(4-chlorophenylsulfanyl)-2-methyl-4-nitro-1H-indole, 2.9 g (81%) as a yellow/brown solid.

[3-(4-Chlorophenylsulfanyl)-2-methyl-4-nitro-1H-indol-1-yl]acetic acid, ethyl ester: Method A

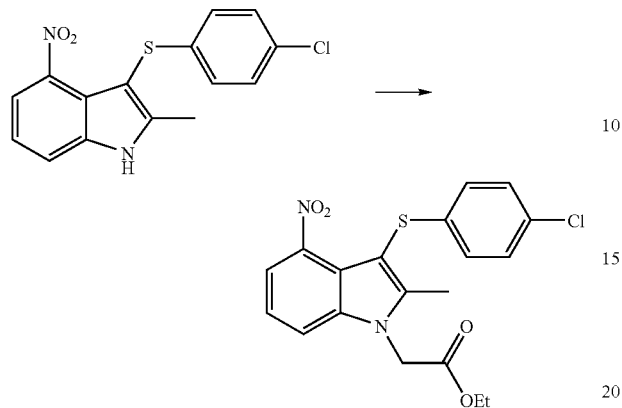

3-(4-Chlorophenylsulfanyl)-2-methyl-4-nitro-1H-indole (3.76 kg, 11.8 mol) and potassium carbonate (1.80 kg, 13.0 mol) were suspended in acetonitrile (32.7 kg). Water (0.53 kg) and a solution of ethyl bromoacetate (2.17 kg, 13.0 mol) in acetonitrile (5.75 kg) were added followed by an acetonitrile line rinse (2.97 kg). The mixture was heated at 50° C. for 6 hours then allowed to cool to 20° C. and held at this temperature overnight. Water (35.4 kg) was added to the reaction mixture and stirring continued for 30 minutes at 15° C. The solid product was collected by filtration, washed with acetonitrile (2.95 kg) then dried in a vacuum oven at 40° C. to afford [3-(4-chlorophenylsulfanyl)-2-methyl-4-nitro-1H-indol-1-yl]acetic acid, ethyl ester as a bright yellow solid, 4.33 kg (91%).

$^1$H NMR (300 MHz, D$_6$-DMSO) δ 7.97 (dd, J=8.3, 0.8 Hz, 1H), 7.65 (dd, J=7.9, 0.8 Hz, 1H), 7.34 (t, J=8.1 Hz, 1H), 7.26 (m, 2H), 6.92 (m, 2H), 5.40 (s, 2H), 4.19 (q, J=7.0 Hz, 2H), 2.45 (s, 3H), 1.22 (t, J=7.1 Hz, 3H).

LC-MS (ES$^+$): 405 (100%, MH$^+$), 407 (MH$^+$).

[4-Acetylamino-3-(4-chlorophenylsulfanyl)-2-methyl-1H-indol-1-yl]acetic acid, ethyl ester: method A

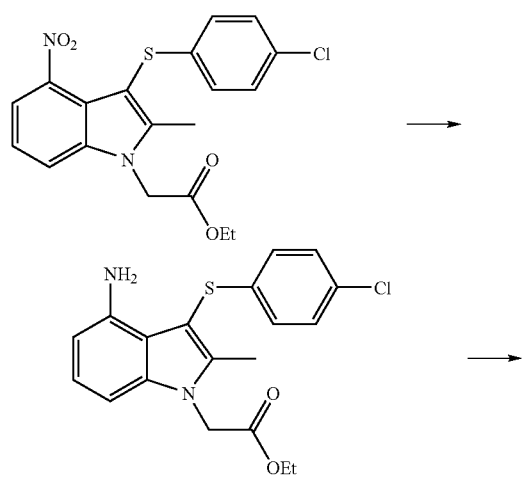

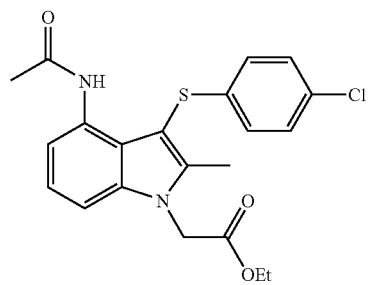

A solution of [3-(4-chlorophenylsulfanyl)-2-methyl-4-nitro-1H-indol-1-yl]acetic acid, ethyl ester (1.99 kg, 4.92 mol) in ethyl acetate (24.2 kg) was hydrogenated in the presence of a 1% Pt/C catalyst paste (1.39 kg 44% w/w) under 4 bar A hydrogen pressure. After 2 hours hydrogen uptake had ceased so the reaction mixture was inerted then filtered through Celite (2.60 kg). The solids were washed with ethyl acetate (3×8 kg) and the combined filtrates distilled until a volume of 26 L remained to leave a solution of [4-amino-3-(4-chlorophenylsulfanyl)-2-methylindol-1-yl]acetic acid, ethyl ester in ethyl acetate. This solution was cooled to 4° C. then triethylamine (0.50 kg, 4.94 mol) added, followed by an ethyl acetate line wash (0.82 kg). A solution of acetyl chloride (0.39 kg, 4.97 mol) in ethyl acetate (3 kg) was added followed by an ethyl acetate line wash (0.76 kg). The reaction mixture was heated at 40° C. for 17 hours then water (16.9 kg) added. The reaction mixture was distilled down until 24.6 kg of distillate had been removed then cooled to 20° C. The solid product was collected by filtration, washed with water (1.9 kg) followed by acetonitrile (1.6 kg) then dried in a vacuum oven at 40° C. to afford [4-acetylamino-3-(4-chlorophenylsulfanyl)-2-methyl-1H-indol-1-yl]acetic acid, ethyl ester, 1.69 kg (82%) as an off white solid.

$^1$H NMR (300 MHz, DMSO) δ 9.51 (s, 1H), 7.46 (d, J=7.5 Hz, 1H), 7.36-7.25 (m, 3H), 7.11 (t, J=8.0 Hz, 1H), 6.97 (d, J=8.7 Hz, 2H), 5.24 (s, 2H), 4.18 (q, J=7.1 Hz, 2H), 2.39 (s, 3H), 1.86 (s, 3H), 1.21 (t, J=7.1 Hz, 3H).

LC-MS (ES$^+$): 417 (100%, MH$^+$), 419 (MH$^+$).

[4-Acetylamino-3-(4-chlorophenylsulfanyl)-2-methyl-1H-indol-1-yl]acetic Acid

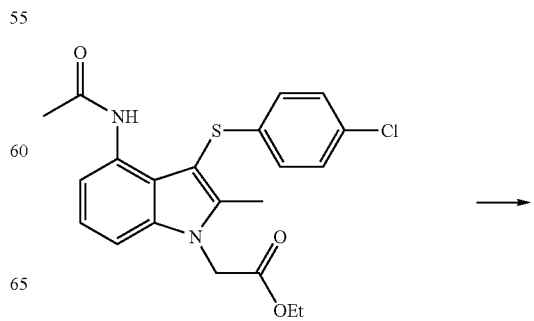

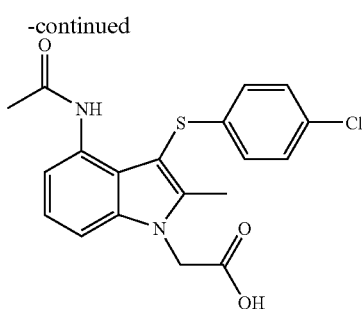

Aqueous sodium hydroxide (1 M, 11.7 kg) was added to a solution of [4-acetylamino-3-(4-chlorophenylsulfanyl)-2-methyl-1H-indol-1-yl]acetic acid, ethyl ester (2.20 kg, 5.28 mol) in 1-propanol (8.2 kg) and the mixture heated to 68° C. After cooling to 40° C., the solution was filtered, the filter rinsed with water (1 kg) then methyl isobutyl ketone (17.8 kg) was added to the filtrate, which was re-heated to 80° C. Aqueous hydrochloric acid (1 M, 12.2 kg) was added over a period of 90 minutes then the mixture cooled to 19° C. The crystalline solid was collected by filtration, washed with water (2×4 kg), ethyl acetate (6 kg) then dried in a vacuum oven at 40° C. to provide [4-acetylamino-3-(4-chlorophenylsulfanyl)-2-methyl-1H-indol-1-yl]acetic acid as white crystals, 1.87 kg (91%).

$^1$H NMR (400 MHz, D$_6$-DMSO) δ 9.51 (s, 1H), 7.47 (d, J=7.6 Hz, 1H), 7.38-7.24 (m, 3H), 7.11 (t, J=8.1 Hz, 1H), 6.98 (d, J=8.5 Hz, 2H), 5.12 (s, 2H), 2.40 (s, 3H), 1.86 (s, 3H).

LC-MS (ES$^+$): 389 (100%, MH$^+$), 391 (MH$^+$).

(4-Nitro-2-methyl-1H-indol-1-yl)-acetic acid, ethyl ester

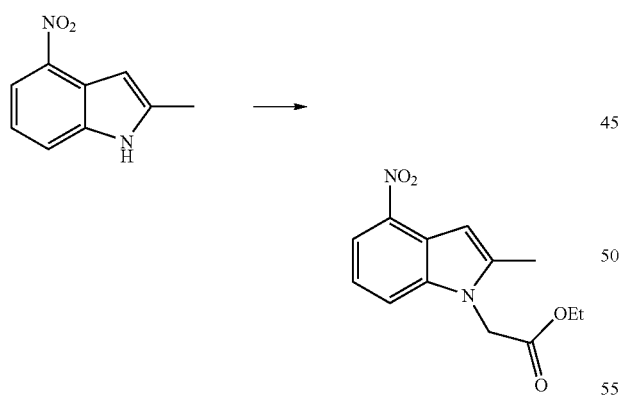

Water (4.5 ml), potassium carbonate (25.9 g, 187 mmol) and ethyl bromoacetate (20.8 ml, 188 mmol) were added sequentially to a suspension of 2-methyl-4-nitro-1H-indole (30 g, 170 mmol) in acetonitrile (225 ml) and the mixture heated at 60° C. for 16 hours. After allowing to cool to ambient temperature, water (225 ml) was added and the resulting mixture was broken up and then filtered. The solid was washed with water (2×75 ml), followed by IMS (2×75 ml) then dried in a vacuum oven to give (4-nitro-2-methyl-1H-indol-1-yl)-acetic acid, ethyl ester, 32.15 g (72%).

$^1$H-NMR (300 MHz, D$_6$-DMSO) δ 8.04 (d, J=8.1 Hz, 1H), 7.93 (d, J=8.1 Hz, 1H), 7.27 (t, J=8.1 Hz, 1H), 6.93 (s, 1H), 5.25 (s, 2H), 4.17 (q, J=7.1 Hz, 2H), 2.44 (s, 3H), 1.21 (t, J=7.1 Hz, 3H)

LC-MS (ES$^+$): 263 (100%, MH$^{30}$)

[3-(4-Chlorophenylsulfanyl)-2-methyl-4-nitro-1H-indol-1-yl]acetic acids ethyl ester: method B Trichloroisocyanuric acid (0.30 g, 1.3 mmol) was added to a solution of bis(p-chlorophenyl)disulphide (1.08 g, 3.8 mmol) in ethyl acetate (10 ml) at ambient temperature resulting in formation of a yellow suspension. After stirring for 30 minutes at this temperature, a slurry of (4-nitro-2-methyl-1H-indol-1-yl)-acetic acid, ethyl ester (2.0 g, 7.6 mmol) in ethyl acetate (10 ml) was added followed by an ethyl acetate rinse (4 ml), using water bath cooling to control the mild exotherm. Stirring was continued for 35 minutes at ambient temperature. Aqueous sodium bicarbonate (5%, 20 ml) was added followed by water (20 ml). After stirring for 45 minutes, ethyl acetate was removed by evaporation, the solid product collected by filtration, washed with water (2×10 ml), followed by 50% v/v aqueous acetonitrile (2×10 ml) then dried overnight in a vacuum oven at 45° C. to provide [3-(4-chlorophenylsulfanyl)-2-methyl-4-nitro-1H-indol-1-yl]acetic acid, ethyl ester as a bright yellow solid, 2.95 g (96%).

4-Amino-2-methyl-1H-indol-1-yl)-acetic acid, ethyl ester

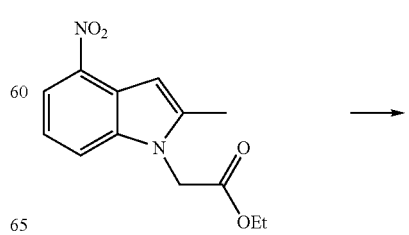

-continued

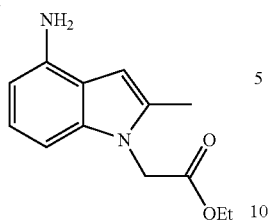

A solution of (4-nitro-2-methyl-1H-indol-1-yl)-acetic acid, ethyl ester (5.0 g, 19 mmol) in ethyl acetate (75 ml) was hydrogenated under 3 bar hydrogen pressure in the presence of a wet 1% Pt/C catalyst paste (38 w/w, 0.7 g) until hydrogen uptake ceased (3 hours). The reaction mixture was filtered through kieselguhr and the solids washed with ethyl acetate (75 ml). The filtrate and wash were combined with solutions obtained from 2 previous experiments which had been carried out in a similar mainer, each on a 2 g scale, and evaporated to dryness to provide (4-amino-2-methyl-1H-indol-1-yl)-acetic acid, ethyl ester, 8.59 g, >100% as a brown oil which solidified on standing.

$^1$H NMR (300 MHz, D$_6$-DMSO) δ 6.73 (t, J=7.9 Hz, 1H), 6.49 (d, J=8.1 Hz, 1H), 6.28 (s, 1H), 6.15 (d, J=7.5 Hz, 1H), 5.05 (br s, 2H), 4.89 (s, 2H), 4.13 (q, J=7.1 Hz, 2H), 2.27 (s, 3H), 1.20 (t, J=7.1 Hz, 3H).

LC-MS (ES$^+$): 233 (100%, MH$^+$).

(4-Acetylamino-2-methyl-1H-indol-1-yl)-acetic acid ethyl ester

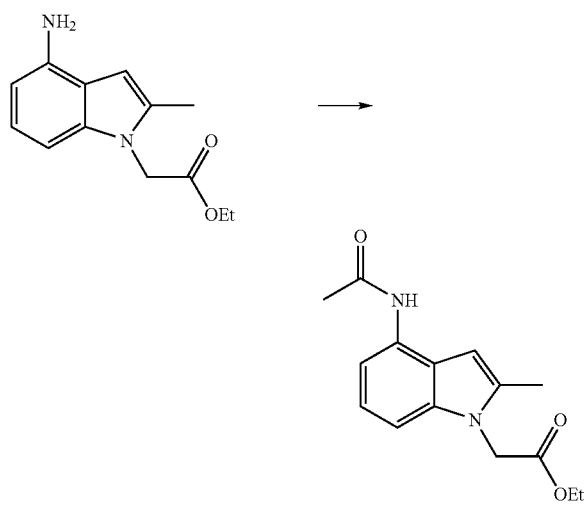

The (4-amino-2-methyl-1H-indol-1-yl)-acetic acid, ethyl ester prepared above (8.59 g) was dissolved in ethyl acetate (175 ml) then triethylamine (5.2 ml, 37 mmol) added followed by acetyl chloride (2.6 ml, 37 mmol). An exotherm to 35° C. was observed and a thick suspension resulted. After stirring for 4 hours during which the mixture was allowed to cool back to ambient temperature, water (85 ml) was added and the ethyl acetate removed by evaporation under vacuum. The solid was collected by filtration, washed with water (25 ml) followed by 50% v/v aqueous acetonitrile (50 ml) then dried in a vacuum oven at 50° C. overnight to provide (4-acetylamino-2-methyl-1H-indol-1-yl)-acetic acid, ethyl ester, as an off-white solid, 7.26 g (77% from (4-nitro-2-methyl-1H-indol-1-yl)-acetic acid, ethyl ester).

$^1$H NMR (300 MHz, D$_6$-DMSO) δ 9.51 (s, 1H), 7.55 (d, J=7.7 Hz, 1H), 7.07 (d, J=8.1 Hz, 1H), 6.96 (t, J=7.9 Hz, 1H), 6.50 (s, 1H), 5.02 (s, 2H), 4.14 (q, J=7.1 Hz, 2H), 2.33 (s, 3H), 2.12 (s, 3H), 1.20 (t, J=7.1 Hz, 3H).

LC-MS (ES$^+$): 275 (100%, MH$^+$).

[4-Acetylamino-3-(4-chloro-phenylsulfanyl)-2-methyl-1H-indol-1-yl]-acetic acid, ethyl ester: method B

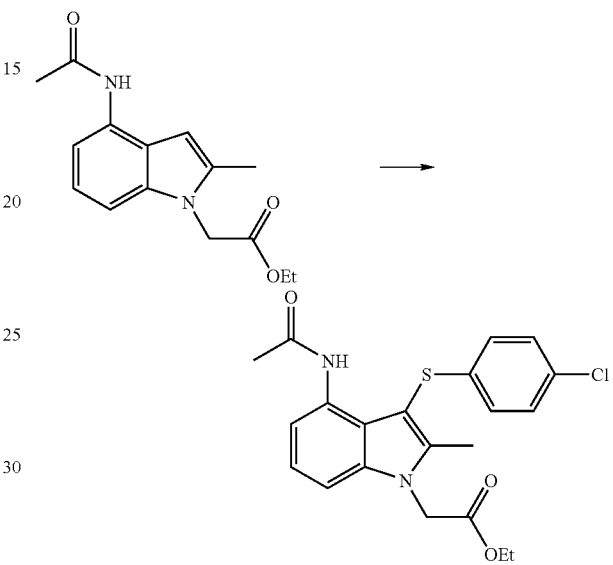

Trichloroisocyanuric acid (0.15 g, 0.65 mmol) was added to a solution of bis(p-chlorophenyl)disulphide (0.55 g, 1.9 mmol) in ethyl acetate (5.25 ml) at ambient temperature resulting in formation of a yellow suspension. After stirring for 15 minutes at this temperature, a slurry of (4-acetylamino-2-methyl-1H-indol-1-yl)-acetic acid, ethyl ester (1.05 g, 3.8 mmol) in ethyl acetate (5.25 ml) was added, followed by an ethyl acetate rinse (2 ml), using water bath cooling to control the mild exotherm. Stirring was continued for 1 h 15 minutes at ambient temperature. Aqueous sodium bicarbonate (5%, 10.5 ml) was added followed by water (10.5 ml). After stirring for 35 minutes, the solid product was collected by filtration, washed with water (2×5 ml) then dried in a vacuum oven at 45° C. overnight to give [4-acetylamino-3-(4-chlorophenylsulfanyl)-2-methyl-1H-indol-1-yl]-acetic acid, ethyl ester as a grey solid, 1.13 g, 71%).

(4-Acetylamino-2-methyl-1H-indol-1-yl)acetic acid

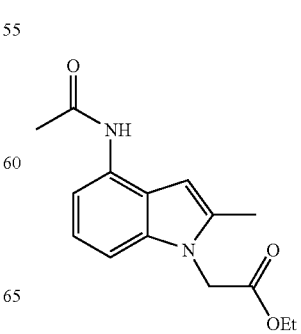

-continued

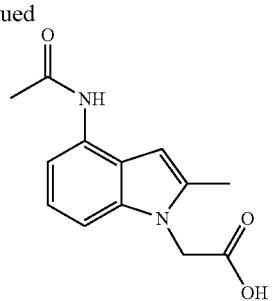

(4-Acetylamino-2-methyl-1H-indol-1-yl)-acetic acid, ethyl ester (2.0 g, 7.3 mmol) was slurried in ethanol (10 ml) at ambient temperature. Aqueous sodium hydroxide (1 M, 10 ml, 10 mmol) was added and the mixture heated to 50° C. The solution obtained at was then allowed to cool back to ambient temperature and aqueous hydrochloric acid (1 M, 11 ml, 11 mmol) added. The resulting solid was collected by filtration, washed with water (2×10 ml) then dried in a vacuum oven at 45° C. overnight to provide (4-acetylamino-2-methyl-1H-indol-1-yl)acetic acid as an off-white solid, 1.66 g (92%).

$^1$H NMR (300 MHz, D$_6$-DMSO) δ 12.97 (s, 1H), 9.49 (s, 1H), 7.54 (d, J=7.5 Hz, 1H), 7.07 (d, J=8.1 Hz, 1H), 6.95 (t, J=7.9 Hz, 1H), 6.49 (s, 1H), 4.91 (s, 2H), 2.33 (d, J=0.8 Hz, 3H), 2.12 (s, 3H)

LC-MS (ES$^+$): 247 (100%, MH$^+$).

[4-Acetylamino-3-(4-chlorophenylsulfanyl)-2-methyl-1H-indol-1-yl]acetic Acid: method B

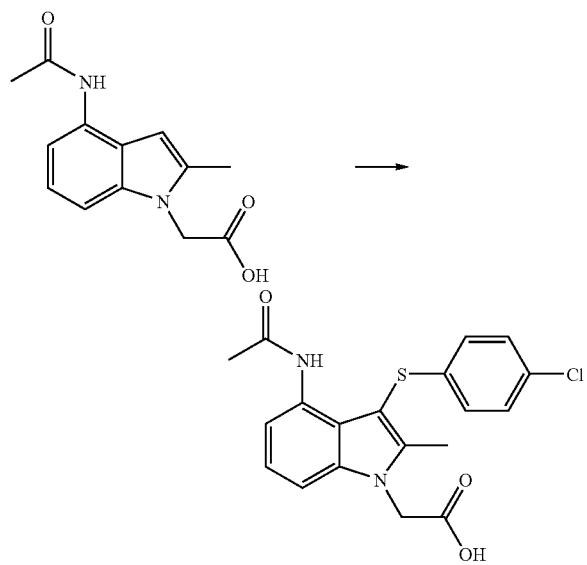

Trichloroisocyanuric acid (0.13 g, 0.56 mmol) was added to a solution of bis(p-chlorophenyl)disulphide (0.47 g, 1.6 mmol) in ethyl acetate (5 ml) at ambient temperature resulting in formation of a yellow suspension. After stirring for 15 minutes at this temperature, a slurry of (4-acetylamino-2-methyl-1H-indol-1-yl)acetic acid (0.80 g, 3.2 mmol) in ethyl acetate (10 ml) was added followed by an ethyl acetate rinse (5 ml), using water bath cooling to control the mild exotherm. Stirring was continued for 1 h 15 minutes at ambient temperature. The solid product was collected by filtration, washed with ethanol (2×10 ml) then dried overnight in a vacuum oven at 45° C. to provide [4-acetylamino-3-(4-chlorophenylsulfanyl)-2-methyl-1H-indol-1-yl]acetic acid as an off-white solid, 1.22 g (97%).

EXAMPLE 2

(2-Methyl-4-nitro-1H-indol-1-yl)acetic acid

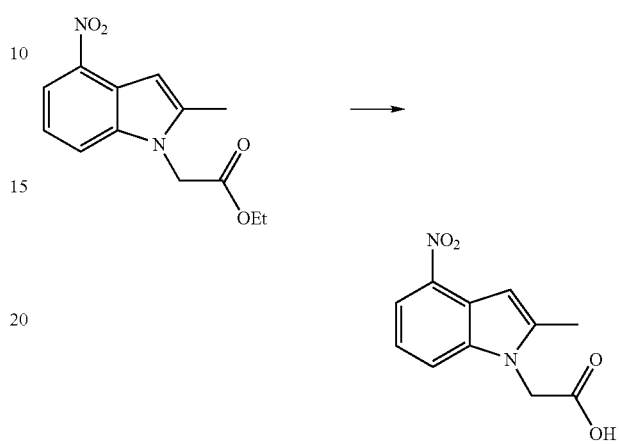

Aqueous sodium hydroxide (1 M, 25 ml) was added to a solution of (4-nitro-2-methyl-1H-indol-1-yl)acetic acid, ethyl ester (5.0 g, 18.9 mmol) in ethanol (25 ml) and the mixture warmed to 40° C. After stirring for 70 mins at this temperature, the mixture was allowed to cool back to ambient temperature and aqueous hydrochloric acid (1 M, 27.5 ml) added causing precipitation of a solid. This was collected by filtration, washed with water (2×25 ml) then dried in a vacuum oven at 50° C. overnight to leave (2-methyl-4-nitro-1H-indol-1-yl)acetic acid as a yellow solid, 4.18 g (94%).

$^1$H-NMR (300 MHz, D$_6$-DMSO) δ 13.2 (s, 1H), 8.03 (d, J=8.1 Hz, 1H), 7.93 (d, J=8.1 Hz, 1H), 7.26 (t, J=8.1 Hz, 1H), 6.92 (s, 1H), 5.13 (s, 2H), 2.45 (s, 3H)

LC-MS (ES$^+$): 235 (100%, MH$^+$)

[3-(4-Chlorophenylsulfanyl)-2-methyl-4-nitro-1H-indol-1-yl]acetic acid

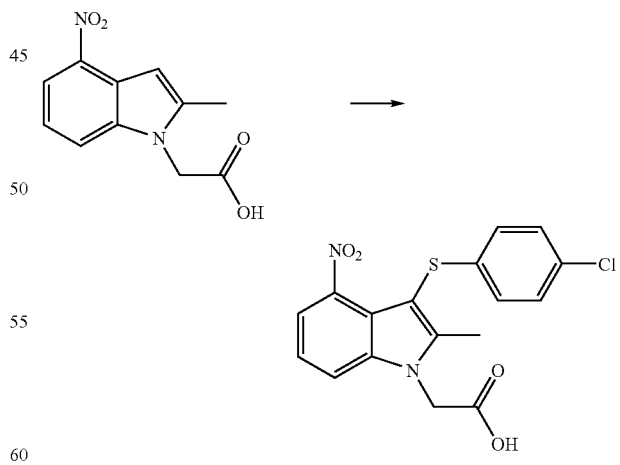

Trichloroisocyanuric acid (0.51 g, 2.2 mmol) was added to a solution of bis(p-chlorophenyl)disulphide (1.84 g, 6.4 mmol) in ethyl acetate (15 ml) at ambient temperature resulting in formation of a yellow suspension. After stirring for 5 minutes at this temperature, a slurry of (4-nitro-2-methyl-1H-indol-1-yl)-acetic acid (3.0 g, 12.8 mmol) in ethyl acetate (30 ml) was added followed by an ethyl acetate rinse (6 ml).

Stirring was continued for 40 minutes at ambient temperature. The solid product was collected by filtration, washed with ethyl acetate (2×10 ml) then dried overnight in a vacuum oven at 50° C. to provide [3-(4-chlorophenylsulfanyl)-2-methyl-4-nitro-1H-indol-1-yl]acetic acid as a bright yellow solid, 2.93 g. The by-product, cyanuric acid, was not removed during the work up.

¹H NMR (300 MHz, D₆-DMSO) δ 13.4 (s, 1H), 7.97 (dd, J=8.3, 0.8 Hz, 1H), 7.64 (dd, J=7.7, 0.8 Hz, 1H), 7.34 (t, J=8.1 Hz, 1H), 7.25 (m, 2H), 6.92 (m, 2H), 5.28 (s, 2H), 2.45 (s, 3H).

LC-MS (ES⁺): 377 (100%, MH⁺), 379 (MH⁺).

The product can be converted to a compound of formula (I) by reduction of the nitro group followed by amide formation using a process analogous to that given above for [4-Acetylamino-3-(4-chlorophenylsulfanyl)-2-methyl-1H-indol-1yl]acetic acid, ethyl ester: method A

The invention claimed is:

1. A process for the preparation of a compound of formula (I) or (II):

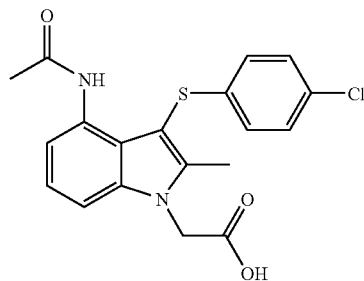

(I)

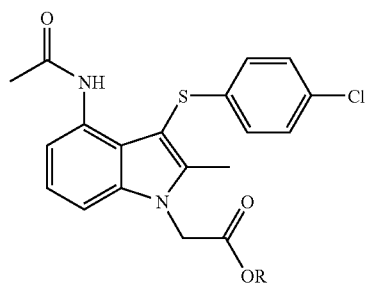

(II)

in which R is an ester forming group, which comprises reaction of a compound of formula (VIII):

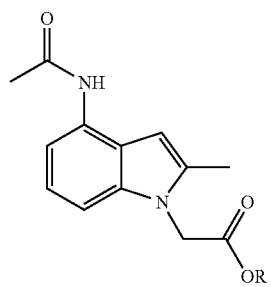

(VIII)

in which R is hydrogen or an ester forming group, by reacting with a compound of formula (VII):

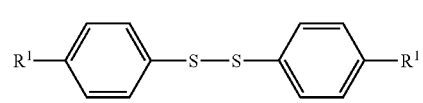

(VII)

in which R¹ is chloro, and optionally thereafter forming a pharmaceutically acceptable salt.

2. A process for the preparation of a compound of formula (II) or the corresponding carboxylic acid:

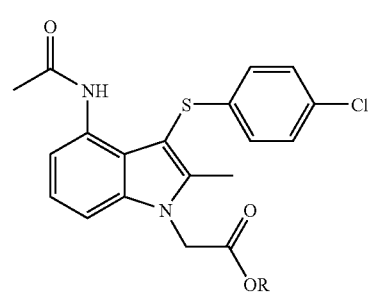

(II)

in which R is hydrogen or an ester forming group, which comprises reducing a compound of formula (III):

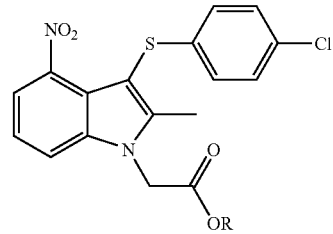

(III)

in which R is hydrogen or an ester forming group with sodium dithionite or by hydrogenation followed by amide formation.

3. A process for the preparation of a compound of formula (III):

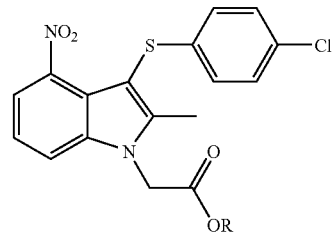

(III)

in which R is hydrogen or an ester forming group, which comprises reaction of a compound of formula (IX):

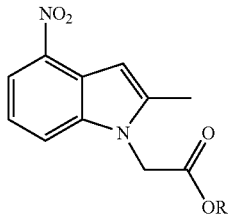
(IX)

in which R is as defined above with a compound of formula (VII):

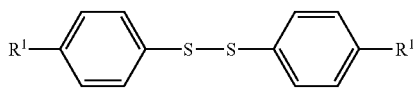
(VII)

in which $R^1$ is chloro.

4. A compound of formula (IX):

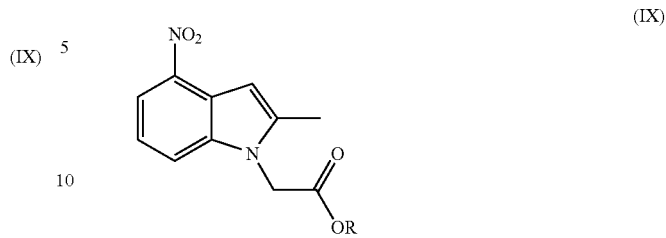
(IX)

in which R is hydrogen, phenyl, benzyl or $C_{1-6}$ alkyl.

5. A process according to claim 1 or claim 3 in which R is $C_{1-6}$ alkyl.

6. A process according to claim 1 or claim 3 in which R is ethyl.

7. A process according to claim 1 or claim 3 which is carried out in sodium methoxide in methanol at elevated temperature.

8. A process according to claim 1 or claim 3 which is carried out using trichloroisocyanuric acid in ethyl acetate or dichloromethane.

\* \* \* \* \*